United States Patent [19]
D'Amico

[11] 3,993,468
[45] Nov. 23, 1976

[54] USE OF 3-SUBSTITUTED BENZOTHIAZOLINES AS PLANT GROWTH REGULANTS

[75] Inventor: John J. D'Amico, St. Louis, Mo.
[73] Assignee: Monsanto Company, St. Louis, Mo.
[22] Filed: May 12, 1975
[21] Appl. No.: 576,512

[52] U.S. Cl. .............................. 71/90; 71/74; 71/76; 260/304 R
[51] Int. Cl.² ............................. A01N 9/12
[58] Field of Search ................. 71/90, 76

[56] References Cited
FOREIGN PATENTS OR APPLICATIONS
21,378   6/1971   Japan
10,182   3/1973   Japan Primary Examiner—Lewis Gotts
Assistant Examiner—Catherine L. Mills
Attorney, Agent, or Firm—Richard H. Shear; Donald W. Peterson

[57] ABSTRACT

Effective plant growth regulaton is obtained by application to the plant of certain benzothiazoline compounds having the formula

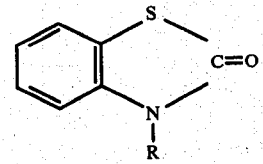

7 Claims, No Drawings

USE OF 3-SUBSTITUTED BENZOTHIAZOLINES AS PLANT GROWTH REGULANTS

This invention relates to the regulation of plant growth by application of an effective amount of certain benzothiazoline compounds to the plant. More particularly, this invention is concerned with a method for increasing the yield of various plants by subjecting said plants to chemical treatment. Specifically, it has been found that such a chemical treatment increases the yield of harvestable leguminous plants as well as the yield of sucrose in sugar-bearing plants.

The term "plant regulant" or "plant growth regulant", as employed in this application, connotes a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

The term "sugar-bearing plants" as used herein means those crops from which sugar or sucrose is usually extracted. Specifically to be included among those sugar-bearing plants are sugar beets and sugar cane.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alteration, increased branching, tillering, terminal inhibition, increased flowering or fruit set, increased root growth, stool or sprout inhibition, delayed budding, defoliation, desiccation, delayed senescence, prolonged dormancy, increased cold hardiness, delayed or accelerated ripening, thinning of fruit, prevention of pre-harvest fruit drop and the like.

Modifications in the normal sequential development of a treated plant to agricultural maturity may also be manifested by reduced transpiration or increased carbohydrate deposition or protein content.

It is to be understood that the regulation of plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

It is presently known that certain benzothiazyl compounds possess herbicidal activity. U.S. Pat. No. 3,069,429 discloses the use of derivatives of 4-halogeno-2-oxobenzothiazolin-3-ylacetic acid to kill weeds. U.S. Pat. No. 3,651,074 discloses the use of certain 2-oxo-3-benzothiazolines as a herbicide. Neither of these patents, however, disclose the use of the specific benzothiazolines used in accordance with the present invention to regulate the growth of plants. Further, neither of these patents disclose the use of such benzothiazolines to increase the harvestable yield of a plant.

U.S. Pat. No. 2,468,075 does disclose the use of certain benzothiazyl compounds as plant growth regulants, but its preferred activity is limited to acting as an abscission agent. That patent neither discloses the use of the specific compounds used in accordance with the process of the invention, nor does the patentee appreciate the increase in yield that may be obtained when such compounds are applied to either leguminous or sugar-bearing plants.

THE PLANT GROWTH REGULATING COMPOUNDS

The plant growth regulating compounds of the present invention have a chemical structure represented by the following formula

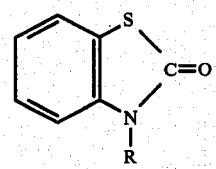

I in which R may be

| | | Compound |
|---|---|---|
| —CH₂CN | (A) | 2-oxo-3-benzothiazoline acetonitrile |
| —CH₂CH₂CH₂CN | (B) | 2-oxo-3-benzothiazoline butyronitrile |
| —CH₂COOCH₃ | (C) | Methyl-2-oxo-3-benzothiazoline acetate |
| —CH(COOC₂H₅)₂ | (D) | Diethyl-2-oxo-benzothiazoline malonate |
| —CH₂COOH | (E) | 2-oxo-3-benzothiazoline acetic acid |
| —CH₂CONH₂ | (F) | 2-oxo-3-benzothiazoline acetamide |
| —CH(COOCH₃)₂ | (G) | Dimethyl-2-oxo-3-benzothizaoline malonate |

These compounds may be prepared in accordance with the following examples.

EXAMPLE 1

PREPARATION OF COMPOUND (A)

A charge containing 75.6 g. (0.5 moles) of 2-benzothiazolol, 33 g. (0.5 moles) of 85% potassium hydroxide and 300 ml. of acetone is stirred for 10 minutes. To the stirred solution is added in one portion 37.2 g. (0.5 moles) of chloroacetonitrile at 40° C. After a temperature rise to 62° C., the stirred reaction mixture is heated at reflux for six hours and then at 25°–30° C. for eighteen hours. After the addition of 700 ml. of water, stirring is continued for 30 minutes at 25°–30° C. The solid is then collected by filtration, washed with water until the washings were neutral to litmus and air-dried at 25°–30° C. The product has a melting point of 134°–135° C.

Anal. Calc'd. for C₉H₆N₂OS: N, 14.73, S, 16.86. Found: N, 14.65, S, 17.01.

EXAMPLE 2

PREPARATION OF COMPOUND (B)

A charge containing 30.2 g. (0.2 mol) of 2-benzothiazolol, 13.2 g. (0.2 mol) of 85% potassium hydroxide, 200 m. of dimethylformamide and 15 ml. of water is stirred for 10 minutes. To the stirred solution at 38° C., 22.8 g. (0.2 mol) of 4-chlorobutyronitrile is added in one portion and then heated at 90°–100° C. for 29 hours. After stirring at 25°–30° C. for 18 hours, 600 ml. of water and 600 ml. of ethyl ether are added and stirring continued for 15 minutes. The separated ether layer is washed with water until the washings were neutral to litmus and dried over sodium sulfate. The ether was removed in vacuo at maximum temperature of 80°–90° C. at 1–2 mm. The product is an amber viscous liquid.

Anal. Calc'd. for $C_{11}H_{10}N_2OS$: N, 12.84, S, 14.69. Found: N, 12.72, S, 14.92.

EXAMPLE 3

PREPARATION OF COMPOUND (C)

To a stirred solution containing 75.5 g. (0.5 moles) of 2-benzothiazolol, 33 g. (0.5 moles) of 85% potassium hydroxide, 300 ml. of methyl alcohol and 20 ml. of water, is added 54.5 g. (0.5 moles) of methyl chloroacetate. After heating at reflux for 5 hours, the stirred reaction mixture is cooled to 25° C. followed by the addition of 500 ml. of water. After stirring at 0°–10° C. for 2 hours, the solid is collected by filtration, washed with water until neutral to litmus and air-dried at 25°–30° C. After recrystallization from isopropyl alcohol, the product melts at 96°–97° C.

Anal. Calc'd. for $C_{10}H_9NO_3S$: N, 6.27, S, 14.36. Found: N, 6.26, S, 14.67.

EXAMPLE 4

PREPARATION OF COMPOUND (D)

Diethyl 2-oxo-3-benzothiazoline malonate is prepared by adding in one portion 59.8 grams (0.25 mole) of bromoethylmalonate to a mixture containing 37.8 grams (0.25 mole) of 2-hydroxybenzothiazole and 16.5 grams (0.25 mole) 85% KOH in 250 ml. of acetone at 30° C. After the addition, the temperature rises to 54° C. The reaction mixture is refluxed for 24 hours at 55°–56° C. After cooling to 25° C., 300 ml. of water and 500 ml. of ethyl ether are added to the reaction mixture and stirred for 15 minutes. The resulting mixture is filtered to remove impurities, and the ether layer of the filtrate recovered. The ether solution is washed with water until neutral and then dried over sodium sulfate. The ether is removed in vacuo at the maximum temperature of 80°–90° C. at 1–2 mm. 53 grams (69% yield) of the desired malonate are recovered as an amber oil. Analysis of the product gives 4.62% nitrogen and 10.8% sulfur compared to 4.53% nitrogen and 10.37% sulfur calculated for $C_{14}H_{15}NO_5S$.

EXAMPLE 5

PREPARATION OF COMPOUND (E)

A stirred charge containing 37.8 g. (0.25 mol) of 2-benzothiazolol, 40 g. (0.25 mol) of 25% aqueous sodium hydroxide and 200 ml. of water is heated to 90° C. and filtered hot to remove a small amount of impurities. To a stirred solution containing 35 g. (0.25 mol) of bromoacetic acid in 100 ml. of water, 18.6 g. (0.125 mol) of potassium carbonate is added in small portions (foaming) until a pH = 8 was obtained. This solution is added to the stirred solution of sodium 2-benzothiazolol and heated at 90°–100° C. for 6 hours and at 25°–30° C. for 18 hours. To this solution, 25 g. of concentrated hydrochloric in 500 ml. of water is added slowly until pH = 2 to 3 is obtained. After stirring, at 0°–10° C. for 30 minutes, the solid was collected by filtration, washed with water until neutral to litmus and air-dried at 45° C. After recrystallization from toluene-/acetone, the product melts at 184°–185° C.

Anal. Calc'd. for $C_9H_7NO_3S$: N, 6.70, S, 15.33. Found: N, 6.75, S, 15.07.

EXAMPLE 6

PREPARATION OF COMPOUND (F)

To a stirred solution containing 30.3 g. (0.2 mol) of benzothiazolol, 13.2 g. (0.2 mol) of 85% potassium hydroxide in 250 ml. of acetone containing 20 ml. of water, 18.7 g. of (0.2 mol) of 2-chloroacetamide is added in one portion. The stirred reaction mixture is heated at reflux for 5.5 hours and at 25°–30° C. for 18 hours. After the addition of 700 ml. of water, stirring is continued at 25°–30° C. for 30 minutes. The solid is collected by filtration, washed with water until the washings were neutral to litmus and air-dried at 25°–30° C. The product has a melting point of 253°–254° C.

Anal. Calc'd. for $C_9H_8N_2O_2S$: N, 13.45; S, 15.40. Found: N, 13.61; S, 15.62.

EXAMPLE 7

PREPARATION OF COMPOUND (G)

To a stirred solution containing 30.3 g. (0.2 mol) of 2-benzothiazolol and 13.2 g. (0.2 mol) of 85% potassium hydroxide in 250 ml. of acetone, 42.2 g. (0.2 mol) of bromomethylmalonate is added in one portion. After the addition, the temperature rises to 49° C. The stirred reaction mixture is refluxed for 24 hours at 55°–56° C. After cooling to 30° C, 400 ml. of water and 600 ml. of ethyl ether are added and stirred for 15 minutes. The separated ether layer is washed with water until the washings were neutral to litmus and air-dried over sodium sulfate. The ether is removed at vacuo at maximum temperature of 30° C. at 1–2 mm. The only solid (46 g.) is air-dried at 25°–30° C. on a porous plate. After recrystallization from alcohol, the product melted at 92°–94° C.

Anal. Calc'd for $C_{12}H_{11}NO_5S$: C, 51.24; H, 3.94; N, 4.98; S, 11.40. Found: C, 51.39; H, 3.98; N, 4.81; S, 11.25;

In selecting the particular compound to be applied to the plant, the definition of the R substituent depends upon whether the plant to be treated is a legume, such as soybean, or a sugar-bearing plant.

Regulation of leguminous plant growth may be accomplished by application to the plant of Compound I wherein R may —$CH_2CN$, —$CH_2CH_2CH_2CN$, —$CH_2COOCH_3$, —$CH(COOC_2H_5)_2$, —$CH_2COOH$, —$CH_2CONH_2$ or —$CH(COOCH_3)_2$.

Regulation of sugar-bearing plants may be accomplished by application to the plant of Compound I wherein R may be —$CH_2CN$, —$CH_2CH_2CH_2CN$, —$CH_2COOCH_3$ or —$CH_2CONH_2$.

THE PLANT GROWTH REGULATING COMPOSITIONS AND METHOD

The term "active ingredient" is used in this specification to describe the active benzothiazolines of the foregoing formula. In practicing the plant growth regulating methods of this invention, the active ingredients can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

When applying the active ingredient to leguminous plants, useful finely divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful in applying the active ingredient to leguminous plants include for example, Stoddard solvent, acetone, alcohols, glycols, and ethyl acetate, benzene and the like. Such leguminous plant growth regulating compositions, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

When the active ingredient is to be applied to sugar-bearing plants, the active ingredient may be admixed with an adjuvant to form a liquid composition or a solid dust composition. Suitable liquid compositions include surfactants such as those enumerated in U.S. Pat. Nos. 3,224,865 and 3,245,775. Preferred surface-active agents which are convenient to use in liquid compositions of this invention are of the non-ionic type such as alkyl phenoxy poly(ethylenoxy)ethanols, polyethylene oxide adducts of fatty and resin acids, and long chain alkyl mercaptan adducts with ethylene oxide. When the sugar-bearing plant to be treated is sugar beets, the preferred surfactant is polyethoxylated nonyl phenol being present at from 0.1 to 0.5 volume percent of the composition. When the plant to be treated is sugar cane, the surfactant preferred is polyethoxylated tallow amine present from 0.05 to 2 volume percent of the composition.

It has been found that desirable modification of leguminous plants is achieved by applying the above-described plant regulants to seeds, emerging seedlings, roots, stems, leaves, flowers, fruits or other plant parts. Such application may be made directly to the plant part, or indirectly by application to the plant growing medium.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. If desired, application of the compositions of the invention to leguminous plants can be accomplished by incorporating the compositions in the soil or other media in the area where modification of the plants is desired.

In selecting the appropriate non-toxic rate of application of the active ingredient to leguminous plants, it will be recognized that precise rates will also be dependent upon the mode of application, such as soil incorporation, band application, pre-plant seed treatment and various other factors known to those skilled in the art. In foliar treatment for the regulation of leguminous plant growth, the active ingredients are applied in amounts from about 0.05 (0.056 kilos/hectare) to about 10 (11.2 kilos/hectare) or more pounds per acre. Foliar applications of from 0.1 to 5 pounds of the active ingredient per acre (0.112 to 5.60 kilos/hectare) are preferred. In applications to the soil habitat of germinant seeds, emerging seedlings, and established vegetation for the regulation of plant growth, the active ingredients are applied in amounts of from about 0.01 to about 20 pounds per acre or more (0.0112 to 22.4 kilos/hectare). Preferably, the active ingredients are applied to the soil at a rate of from 0.1 to 10 pounds per acre (0.112 to 11.2 kilos/hectare). Foliar application to plants beginning to blossom are particularly advantageous and are preferred.

It has been found convenient to apply the compositions to sugar-bearing plants in the form of aqueous emulsions, solutions or suspensions, the dilution being such that a spray volume of from 7 to 20 gallons of liquid per acre (10.6 to 46.2 liters/hectare) will contain the desired dosage of active ingredient. It will be recognized, however, that higher or lower total spray volumes can be beneficially employed depending upon the particular dispersing apparatus and other factors well understood by those skilled in the art.

In determining the appropriate rates and times of application to the sugar-bearing plants, it is necessary to consider both the chronological age of the plant and its stage of maturity. For example, cane, depending upon the practice in different geographical areas, is grown from 9 to about 30 months. Application at a rate of from about 0.1 to 5.0 pounds per acre (0.112 to 5.60 kilos/hectare) can be made from about 2 to 10 weeks prior to the projected harvest date. Preferably, such applications are made from 3 to 7 weeks before said date.

The plant growth regulating compounds of the invention have demonstrated effective regulation of sugar-bearing plants in addition to leguminous plants. The following examples are presented to illustrate the effectiveness of the active ingredient in regulating the growth of sugar-bearing plants and are not intended to limit the scope of the invention.

EXAMPLE 8

In determining the regulatory effects of compounds of this invention on sugar cane, it should be noted that the appropriate rate of application can vary from about 0.1 lb. per acre (0.112 kilos/hectare) to about 5.0 lbs. per acre (5.60 kilos/hectare). Depending upon local cultural practices, it is necessary to consider both the chronological age and the maturity stage of the cane in rate determinations. Application of the treatment to the cane is generally made from about 2 to 10 weeks prior to the scheduled harvest date.

In this test individual sugar cane stalks are treated with compounds of this invention about 4 weeks before harvest. To avoid sampling errors, older cane, preferably 13 to 23 months old, are employed in the tests. For each compound employed, at least 5 stalks are used, processed, and the total values obtained are averaged for each stalk. In order to improve the accuracy of the analyses, only the terminal 15 joints of each stalk are used. An identical number of untreated sugar cane stalks of the same age are similarly processed to provide a control. A comparison of the values obtained for the treated cane with the control sample provides a convenient means of determining the regulatory effectiveness of these compounds.

The analyses are carried out by the press method developed by T. Tanimoto and reported in *Hawaiian Planters' Record*, Volume 57, pp. 133–150. The data are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugar cane juice.

About 38 mg. of 2-oxo-3-benzothiazoline-acetonitrile employed is dissolved in a small amount of water which contains about 0.5% of a surface active agent. The resultant solution is then applied to the tip of each of the stalks to be tested with the exception of the untreated controls. After harvest, the top 15 joints of each stalk of a treated group are removed, combined and analyzed as described. Results are summarized in Table 1.

TABLE I

|  | 4 week Harvest | | 5 week Harvest | |
| --- | --- | --- | --- | --- |
|  | Purity | Pol % Cane | Purity | Pol % Cane |
| Treated Cane | 68.88 | 7.50 | 78.80 | 11.19 |
| Control | 64.25 | 6.63 | 65.99 | 6.85 |

EXAMPLE 9

A number of sugar beet plants are grown from seeds in the greenhouse for a period of approximately eight weeks. Prior to testing the plants are thinned to one plant per pot and selected for uniformity. One set of three plants are sprayed per treatment by a composition containing the active ingredient. The composition is formulated in accordance with Table II in which the stock solution is 100 mg. of active ingredient dissolved in 1 ml. of solvent.

TABLE II

| RATE Lb/Acre (kilos/hectare) | ml of solution in 40 ml spray volume (for six plants) | | | ml of Ethomeen Solvent |
| --- | --- | --- | --- | --- |
|  | mg/plant | ml Stock Solution | ml Solvent |  |
| 1.0 (1.12) | 15 | 0.9 | 9.1 | 30 |
| 0.5 (0.56) | 7.5 | 0.45 | 9.55 | 30 |
| 0.1 (0.112) | 1.5 | 0.9* | 9.1 | 30 |
| 0.05 (0.056) | 0.75 | 0.45* | 9.55 | 30 |
| 0.01 (0.012) | 0.15 | 0.9** | 9.1 | 30 |

*Stock solution diluted 1:10
**Stock solution diluted 1:100

3 weeks after spraying the plants are observed and the results tabulated.

Table II illustrated the results obtained when compared to the untreated control plants. The coefficient of variation (C.V.) for the untreated controls of each test is listed as well.

TABLE III

| Active Ingredient | RATE Lb/Acre (kilos/hectare) | Percent Change from Control | |
| --- | --- | --- | --- |
|  |  | % Sucrose | C.V. |
| 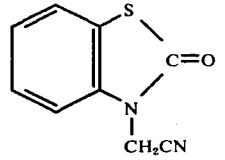 | 0.05 (0.056) | + 8 | 3 |
|  | 0.1 (0.112) | + 3 | 3 |
|  | 0.1 (0.112) | + 11 | 10 |
|  | 0.5 (0.56) | 0 | 10 |
|  | 0.5 (0.56) | + 4 | 3 |
| 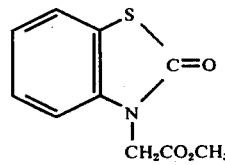 | 0.01 (0.0112) | + 9 | 9 |
|  | 0.03 (0.0336) | + 7 | 9 |
|  | 0.06 (0.0672) | − 2 | 9 |
|  | 0.06 (0.0672) | − 23 | 8 |
|  | 0.3 (0.336) | − 31 | 8 |
| 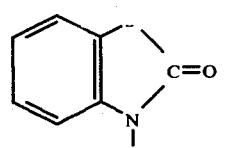 | 1.2 (1.34) | + 7 | 6 |
|  | 6.0 (6.72) | 0 | 6 |

As illustrated by the above examples, application of the active ingredient to sugar-bearing plants enhances the yield of sucrose obtained. A preferred embodiment of the invention encompasses the application of compound (A) to sugar cane.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for enhancing the sucrose content of sugar-bearing plants which comprises treating said sugar-bearing plants with an effective amount of a compound of the formula

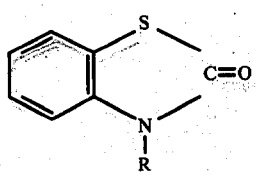

wherein R is selected from the group consisting of —CH$_2$CN, —(CH$_2$)$_3$CN, —CHCOOCH$_3$ and —CH$_2$CONH$_2$.

2. The method of claim 1 wherein said compound is 2-oxo-3-benzothiazoline acetonitrile.

3. The method of claim 1 wherein said compound is 2-oxo-3-benzothiazoline butyronitrile.

4. The method of claim 1 wherein said compound is methyl-2-oxo-3-benzothiazoline acetate.

5. The method of claim 1 wherein said compound is 2-oxo-3-benzothiazoline acetamide.

6. The method of claim 1 wherein said sugar-bearing plants are sugar cane.

7. The method of claim 6 wherein said compound is applied to said sugar cane from about 2 to 10 weeks prior to harvest.

* * * * *